(12) United States Patent
Shohat et al.

(10) Patent No.: US 8,480,647 B2
(45) Date of Patent: Jul. 9, 2013

(54) DELIVERY DEVICE FOR DELIVERING BIOACTIVE AGENTS TO INTERNAL TISSUE IN A BODY

(75) Inventors: Shaul Shohat, Kfar HaOranim (IL); Eli Machlev, ShaAr Ephraim-Doar-Na Lev HaSharon (IL); Dana Haimovich, Kiryat-Haim (IL); Abraham J. Domb, Efrat (IL)

(73) Assignee: Bioprotect Ltd., Kfar-Saba (IL)

( * ) Notice: Subject to any disclaimer, the term of this patent is extended or adjusted under 35 U.S.C. 154(b) by 809 days.

(21) Appl. No.: 12/599,823

(22) PCT Filed: May 13, 2008

(86) PCT No.: PCT/IL2008/000662
§ 371 (c)(1),
(2), (4) Date: Nov. 12, 2009

(87) PCT Pub. No.: WO2008/139473
PCT Pub. Date: Nov. 20, 2008

(65) Prior Publication Data
US 2011/0295226 A1    Dec. 1, 2011

Related U.S. Application Data

(60) Provisional application No. 60/924,401, filed on May 14, 2007.

(51) Int. Cl.
*A61M 31/00* (2006.01)
*A61M 29/00* (2006.01)

(52) U.S. Cl.
USPC .................... 604/500; 604/103.01

(58) Field of Classification Search
USPC .................... 604/500, 506, 103.01
See application file for complete search history.

(56) References Cited

U.S. PATENT DOCUMENTS

| | | | |
|---|---|---|---|
| 4,513,058 A | 4/1985 | Martin | |
| 5,176,692 A | 1/1993 | Wilk et al. | |
| 5,318,586 A | 6/1994 | Ereren et al. | |
| 5,334,210 A | 8/1994 | Gianturco et al. | |
| 5,336,252 A * | 8/1994 | Cohen | 607/119 |
| 5,458,612 A | 10/1995 | Chin | |
| 5,516,522 A | 5/1996 | Peyman et al. | |
| 5,547,472 A * | 8/1996 | Onishi et al. | 604/103.01 |

(Continued)

FOREIGN PATENT DOCUMENTS

| | | |
|---|---|---|
| DE | 102007018341 | 10/2008 |
| DE | 102007051782 | 5/2009 |

(Continued)

OTHER PUBLICATIONS

Restriction Official Action Dated Dec. 12, 2011 From the US Patent and Trademark Office Re. U.S. Appl. No. 12/531,073.

(Continued)

*Primary Examiner* — Kevin C Sirmons
*Assistant Examiner* — Michael J Anderson

(57) ABSTRACT

A device and method for administering a bioactive agent to internal tissue in a body, by introducing a balloon in a deflated condition into the body, inflating the balloon, introducing the bioactive agent into the balloon at the time of, after, or before the inflation of the balloon, and delivering the bioactive agent from the balloon to the tissue.

28 Claims, 5 Drawing Sheets

U.S. PATENT DOCUMENTS

| | | | |
|---|---|---|---|
| 5,641,505 | A | 6/1997 | Bowald et al. |
| 5,653,758 | A | 8/1997 | Daniels et al. |
| 5,720,762 | A | 2/1998 | Bass |
| 5,769,884 | A * | 6/1998 | Solovay ............. 623/1.13 |
| 6,019,781 | A | 2/2000 | Worland |
| 6,102,928 | A | 8/2000 | Bonutti |
| 6,187,023 | B1 | 2/2001 | Bonutti |
| 6,248,131 | B1 | 6/2001 | Felt et al. |
| 6,527,693 | B2 | 3/2003 | Munro, III et al. |
| 6,746,465 | B2 | 6/2004 | Diederich et al. |
| 6,800,082 | B2 | 10/2004 | Rousseau |
| 6,932,834 | B2 | 8/2005 | Lizardi et al. |
| 7,144,398 | B2 | 12/2006 | Chern Lin et al. |
| 7,404,791 | B2 | 7/2008 | Linares et al. |
| 7,601,113 | B2 | 10/2009 | Lebovic et al. |
| 2002/0016626 | A1 | 2/2002 | DiMatteo et al. |
| 2002/0052653 | A1 | 5/2002 | Durgin |
| 2002/0058947 | A1 | 5/2002 | Hochschuler et al. |
| 2003/0028196 | A1 | 2/2003 | Bonutti |
| 2003/0036728 | A1* | 2/2003 | Samson et al. ......... 604/103.01 |
| 2003/0078602 | A1 | 4/2003 | Rousseau |
| 2003/0105469 | A1 | 6/2003 | Karmon |
| 2003/0181939 | A1 | 9/2003 | Bonutti |
| 2004/0038874 | A1 | 2/2004 | Omoigui |
| 2004/0097794 | A1 | 5/2004 | Bonutti |
| 2004/0143285 | A1 | 7/2004 | Bonutti |
| 2004/0254625 | A1 | 12/2004 | Stephens et al. |
| 2004/0267315 | A1 | 12/2004 | Wolf et al. |
| 2005/0245938 | A1 | 11/2005 | Kochan |
| 2005/0251245 | A1* | 11/2005 | Sieradzki et al. ............ 623/1.39 |
| 2005/0273075 | A1* | 12/2005 | Krulevitch et al. ........... 604/509 |
| 2005/0278025 | A1 | 12/2005 | Ku et al. |
| 2006/0100629 | A1 | 5/2006 | Lee |
| 2006/0106361 | A1* | 5/2006 | Muni et al. ................... 604/500 |
| 2006/0147492 | A1 | 7/2006 | Hunter et al. |
| 2006/0149380 | A1 | 7/2006 | Lotz et al. |
| 2006/0182780 | A1* | 8/2006 | Riley et al. .................... 424/426 |
| 2006/0233852 | A1 | 10/2006 | Milbocker |
| 2006/0241766 | A1 | 10/2006 | Felton et al. |
| 2007/0038292 | A1 | 2/2007 | Danielpour |
| 2007/0078477 | A1 | 4/2007 | Heneveld, Sr. et al. |
| 2007/0118218 | A1 | 5/2007 | Hooper |
| 2007/0198022 | A1 | 8/2007 | Lang et al. |
| 2008/0033471 | A1 | 2/2008 | Paz et al. |
| 2008/0269897 | A1 | 10/2008 | Joshi |
| 2009/0112214 | A1 | 4/2009 | Philippon et al. |
| 2010/0023127 | A1 | 1/2010 | Shohat |
| 2010/0069947 | A1 | 3/2010 | Sholev et al. |

FOREIGN PATENT DOCUMENTS

| | | |
|---|---|---|
| EP | 0507645 | 10/1992 |
| JP | 06-510450 | 11/1994 |
| JP | 2003-325685 | 11/2003 |
| JP | 2006-247257 | 9/2006 |
| WO | WO 93/04727 | 3/1993 |
| WO | WO 2005/105172 | 11/2005 |
| WO | WO 2006/001009 | 1/2006 |
| WO | WO 2006/055516 | 5/2006 |
| WO | WO 2006/074879 | 7/2006 |
| WO | WO 2007/002561 | 1/2007 |
| WO | WO 2007/054934 | 5/2007 |
| WO | WO 2007/125060 | 11/2007 |
| WO | WO 2008/111073 | 9/2008 |
| WO | WO 2008/111078 | 9/2008 |
| WO | WO 2008/139473 | 11/2008 |
| WO | WO 2012/017438 | 2/2012 |

OTHER PUBLICATIONS

Translation of Notice of Reason for Rejection Dated Nov. 5, 2010 From the Japanese Patent Office Re. Application No. 2007-517651.
Response Dated Dec. 30, 2011 to the Communication Pursuant to Rules 70(2) and 70a(2) EPC of Jun. 24, 2011 From the European Patent Office Re. Application No. 08738353.5.
Response Dated Dec. 28, 2011 to Supplementary European Search Report and the European Search Opinion of Jun. 6, 2011 From the European Patent Office Re. Application No. 08738353.5.
Communication Relating to the Results of the Partial International Search Dated Nov. 3, 2011 From the International Searching Authority Re. Application No. PCT/IL2011/000637.
International Search Report and the Written Opinion Dated Jan. 9, 2012 From the International Searching Authority Re. Application No. PCT/IL2011/000637.
Notification of Publication of Patent Application for Invention and Entering the Substantive Examination Proceeding Dated Jul. 28, 2010 From the Patent Office of the People's Rebublic of China Re. Application No. 200880024447.5 and Its Translation Into English.
Response Dated Oct. 20, 2010 to Notification of Publication of Patent Application for invention and Entering the Substantive Examination Proceeding of Jul. 28, 2010 From the Patent Office of the People's Rebublic of China Re. Application No. 200880024447.5.
Notification of Publication of Patent Application for Invention and Entering the Substantive Examination Proceeding Dated Oct. 13, 2010 From the Patent Office of the People's Republic of China Re. Application No. 200880015430.3.
Response Dated Jan. 6, 2011 to Notification of Publication of Patent Application for Invention and Entering the Substantive Examination Proceeding Dated Oct. 13, 2010 From the Patent Office of the People's Republic of China Re. Application No. 200880015430.3.
Translation of Office Action Dated Jan. 11, 2011 From the State Intellectual Property Office of the People's Republic of China Re. Application No. 200580028684.5.
International Search Report and the Written Opinion Dated Oct. 23, 2008 From the International Searching Authority Re.: Application No. PCT/IL08/00662.
International Preliminary Report on Patentability Dated Jan. 21, 2010 From the International Bureau of WIPO Re.: Application No. PCT/IL2008/000662.
Response Dated Feb. 27, 2011 to Office Action of Oct. 27, 2009 From the Israel Patent Office Re.: Application No. 180270.
International Preliminary Report on Patentability Dated Jul. 27, 2006 From the International Preliminary Examining Authority Re.: Application No. PCT/IL2005/000672.
Translation of Office Action Dated Oct. 31, 2008 From the State Intellectual Property Office of the People's Republic of China Re.: Application No. 200580028684.5.
Communication Relating to the Results of the Partial International Search Dated Nov. 18, 2005 From the International Searching Authority Re.: Application No. PCT/IL2005/000672.
International Search Report Dated Feb. 22, 2006 From the International Searching Authority Re.: Application No. PCT/IL2005/000672.
Office Action Dated Oct. 27, 2009 From the Israel Patent Office Re.: Application No. 180270 and Its Translation Into English.
Official Action Dated Jun. 8, 2009 From the US Patent and Trademark Office Re.: U.S. Appl. No. 11/630,257.
Official Action Dated Aug. 19, 2009 From the US Patent and Trademark Office Re.: U.S. Appl. No. 11/630,257.
Response Dated Jan. 4, 2010 to Decision of Rejection of Oct. 16, 2009 From the State Intellectual Property Office of the People's Republic of China Re.: Application No. 200580028684.5.
Response Dated Dec. 22, 2009 to Official Action of Aug. 19, 2009 From the US Patent and Trademark Office Re.: U.S. Appl. No. 11/630,257.
Translation of Decision on Rejection Dated Oct. 16, 2009 From the State Intellectual Property Office of the People's Republic of China Re.: Application No. 200580028684.5.
Translation of Office Action Dated Jul. 3, 2009 From the State Intellectual Property Office of the People's Republic of China Re.: Application No. 200580028684.5.
Written Opinion Dated Feb. 22, 2006 From the International Searching Authority Re.: Application No. PCT/IL2005/000672.
Response Dated Apr. 21, 2011 to Notice of Reason for Rejection of Nov. 5, 2010 From the Japanese Patent Office Re. Application No. 2007-517651.
Invitation to Pay Additional Fees Dated Sep. 17, 2008 From the International Searching Authority Re.: Application No. PCT/IL08/00354.

International Preliminary Report on Patentability Dated Jan. 21, 2010 From the International Bureau of WIPO Re.: Application No. PCT/IL2008/000347.
International Preliminary Report on Patentability Dated Oct. 22, 2009 From the International Bureau of WIPO Re.: Application No. PCT/IL2008/000354.
International Search Report Dated Nov. 20, 2008 From the International Searching Authority Re.: Application No. PCT/IL08/00347.
International Search Report Dated Nov. 26, 2008 From the International Searching Authority Re.: Application No. PCT/IL08/00354.
Invitation to Pay Additional Fees Dated Sep. 23, 2008 From the International Searching Authority Re.: Application No. PCT/IL08/00347.
Official Action Dated Apr. 14, 2010 From the US Patent and Trademark Office Re.: U.S. Appl. No. 11/630,257.
Patentability Search on Expandable Prostheses Particularly Useful for Rotator Cuff Protection Dated Oct. 31, 2007 Effectuated by Sol Scheinbein.
Written Opinion Dated Nov. 20, 2008 From the International Searching Authority Re.: Application No. PCT/IL08/00347.
Written Opinion Dated Nov. 26, 2008 From the International Searching Authority Re.: Application No. PCT/IL08/00354.
Third Party Submission Under 37 CFR §1.99 Dated Mar. 26, 2010 in the US Patent and Trademark Office Re.: U.S. Appl. No. 12/531,332.
Supplementary European Search Report and the European Search Opinion Dated Jun. 6, 2011 From the European Patent Office Re. Application No. 08738353.5.
Examiner's Report Dated Apr. 28, 2010 From the Australian Government, IP Australia Re. Application No. 2005257050.
Translation of Official Decision of Rejection Dated Jun. 7, 2011 From the Japanese Patent Office Re. Application No. 2007-517651.
Communication Pursuant to Rules 70(2) and 70a(2) EPC Dated May 24, 2011 From the European Patent Office Re. Application No. 08738353.5.
Response Dated May 12, 2011 to Office Action of Jan. 11, 2011 From the State Intellectual Property Office of the People's Republic of China Re. Application No. 200580028684.5.
Request for Reconsideration Filed With an RCE Dated Aug. 9, 2010 to Official Action of Apr. 14, 2010 From the US Patent and Trademark Office Re.: U.S. Appl. No. 11/630,257.
Communication Pursuant to Article 94(3) EPC Dated Feb. 16, 2012 From the European Patent Office Re. Application No. 08738353.5.
Notice of Allowance Dated Mar. 14, 2012 From the US Patent and Trademark Office Re.: U.S. Appl. No. 11/630,257.
Patent Examination Report Dated Jul. 13, 2012 From the Australian Government, IP Australia Re. Application No. 2008224435.
Restriction Official Action Dated Feb. 6, 2012 From the US Patent and Trademark Office Re. U.S. Appl. No. 12/531,073.
Translation of Office Action Dated Feb. 17, 2012 From the State intellectual Property Office of the People's Republic of China Re. Application No. 200880015430.3.
Translation of Office Action Dated Mar. 28, 2012 From the State Intellectual Property Office of the People's Republic of China Re. Application No. 200880014369.0.
Translation of Office Action Dated Mar. 30, 2012 From the State Intellectual Property Office of the People's Republic of China Re. Application No. 200880024447.5.
Translation of Notice of Payment of the Restoration Fee for Unity of Invention Dated Jul. 26, 2011 From the State Intellectual Property Office of the People's Republic of China Re. Application No. 200880014369.0.
Examiner's Report Dated Apr. 28, 2010 From the Australian Government, IP Australia Re. Application No. 2005257050
Communication Pursuant to Article 94(3) EPC Dated Dec. 1, 2011 From the European Patent Office Re. Application No. 05754685.5.
Translation of Office Action Dated Oct. 19, 2011 From the State Intellectual Property Office of the People's Republic of China Re. Application No. 200880014369.0.
Communication Pursuant to Article 94(3) EPC Dated Dec. 21, 2012 From the European Patent Office Re. Application No. 08738353.5.
Translation of Office Action Dated Dec. 11, 2012 From the State Intellectual Property Office of the People's Republic of China Re. Application No. 200880015430.3.

* cited by examiner

US 8,480,647 B2

DELIVERY DEVICE FOR DELIVERING BIOACTIVE AGENTS TO INTERNAL TISSUE IN A BODY

RELATED APPLICATIONS

This application is a National Phase of PCT Patent Application No. PCT/IL2008/000662 having International filing date of May 13, 2008, which claims the benefit of U.S. Provisional Patent Application No. 60/924,401 filed on May 14, 2007. The contents of the above Applications are all incorporated herein by reference.

FIELD AND BACKGROUND OF THE INVENTION

The present invention relates to delivery devices, and methods, for delivering a bioactive agent to internal tissue in a body. The invention is particularly useful in delivering drugs of large molecular size and/or of fragile structure, such as protein drugs, and is therefore described below with respect to such an application, but it will be appreciated that the method could be used for the delivery of many other types of drugs, as well as other types of bioactive agents, such as herbal medications, homeopathic remedies, and traditional medications.

There is need for a drug delivery system that permits easy incorporation of a large variety of drugs without modification or alteration of the chemical structure and without affecting their activity. This is especially true for hydrophilic water soluble drugs such as proteins and peptides, heparins and oligo and polynucleotides (DNA or RNA) that are generally sensitive to deactivation by mechanisms including denaturation, aggregation, dimerization and chemical modification. The deactivation process may be induced by the use of organic solvents, the interface between water and the organic solvent, mechanical sheer applied, unfavor microenviroment around the active agent such as formation of acidic or basic local pH, high ionic strength and increase in drug concentration.

Protein drugs have been developed for treating hepatitis C, multiple sclerosis, hormonal disorders, and different cancers. However, the use of most protein drugs is limited by the inconvenient and invasive manner in which they must currently be administered. This involves either intravenous infusion or frequent subcutaneous or intramuscular injections throughout the therapy.

Delivering proteins is a challenge because of their large size and fragile three-dimensional structure, which must be maintained for biological activity. As a result, proteins exhibit poor oral bioavailability, eliminating the route by which small molecular weight drugs are most often delivered. A variety of approaches for improved delivery of therapeutic proteins are being explored in academia, government labs, and industry. injectable, biodegradable system that provides a sustained release of the agent over time is desired.

The development of effective systems for the sustained delivery of therapeutic proteins requires that several key obstacles are overcome. These include (i) processing and formulating the protein and delivery system so that the protein's fragile conformation and biological activity are maintained throughout processing and during prolonged release in the body, (ii) controlling the release so that therapeutic levels are maintained for the desired time, and (iii) developing a manufacturing process to produce quantities of sterile material for clinical trials and commercialization. In addition, it is desired that the delivery carrier will be degraded and eliminated from the body after the drug has been released.

A number of processes have been developed for the encapsulation of low molecular weight drugs in biodegradable microspheres by using phase separation, solvent evaporation, emulsion, or spray drying steps. However, the conditions typically used in these processes, such as elevated temperatures, high concentrations of surfactants, or organic and aqueous solvent mixtures, and apply of mechanical forces resulted in accelerated protein degradation. Degradation can decrease potency and increase immunogenicity, which in turn may adversely affect the safety and efficacy of the drug.

Maintaining stability of the protein following injection of a sustained release formulation poses a considerable challenge because proteins in microsphere formulations remain in a concentrated, hydrated state at physiological temperatures for prolonged periods after injection. These conditions are conducive to protein degradation reactions, including physical aggregation, deamidation, and oxidation. Several stabilization strategies can be used to maintain protein integrity under these conditions. The choice of one or more stabilizing agents is determined empirically. One effective approach is to form a complex with a divalent metal cation before encapsulation. Zinc has been employed in this manner to stabilize recombinant human growth hormone (rhGH) and recombinant a-interferon (a-IFN) in microspheres Also, protein stability in hydrated microspheres can be improved by using certain salts. For example, ammonium sulfate has been shown to stabilize erythropoietin during release.

In addition to maintaining protein stability during processing and release, the microsphere formulation must display the release kinetics required to achieve a sustained therapeutic effect. Following injection of the microspheres into the body, the encapsulated protein is released by a complex process involving hydration of the particles, dissolution of the drug, drug diffusion through water-filled pores within the particles, and polymer erosion. Two primary considerations are minimizing how much protein is released immediately (burst) and achieving the desired duration and rate of protein release. The duration of release is governed by the type of PLG polymer used and the addition of release modifying excipients such as zinc carbonate [Y. Zhang et al., *J. Biomed. Mater. Res.* 34, 531 (1997)]. The development of a sustained release system for a therapeutic protein begins with identifying a formulation with satisfactory stability characteristics and kinetics of release in animal models, toxicological and storage stability studies, and then human clinical testing.

Advantages inherent in sustained delivery of proteins are likely to include improved patient compliance (by reducing the need for self-injection), potentially lower costs (by reducing the frequency of visits to a caregiver's office), greater usage of a drug (through new indications and ease of use), and improved safety and efficacy (by reducing variability inherent in frequent injections). For certain proteins, it may also be possible to reduce the total dose per month, thereby reducing the cost to patients. Nevertheless, microsphere-based sustained delivery systems may be limited by the daily dose of protein needed for a therapeutic effect.

Biodegradable injectable in situ forming drug delivery systems represent an attractive alternative to microspheres and implants as parenteral depot systems. Their importance will grow as numerous proteins will lose their patent protection in the near future. These devices may offer attractive opportunities for protein delivery and could possibly extend the patent life of protein drugs. The controlled release of bioactive macromolecules via solid in situ forming systems has a number of advantages, such as ease of administration, less complicated fabrication, and less stressful manufacturing conditions for sensitive drug molecules. However, these systems still safer from non-desired release profile where significant amount of drug is released during the first few days with little in the days after. Also, a release for a few weeks can be achieved for certain short proteins and only days to 2-3 weeks for certain stable proteins. Sensitive proteins are exposed to acidic conditions in the polymer matrix during its degradation which deteriorate the incorporated therapeutic protein.

Alternative approaches for sustained delivery of therapeutic proteins are in various stages of development, there is no polymeric controlled delivery system in clinical use for proteins. There are two PLA based microsphere delivery systems for LHRH and somatostatin short peptides. One more microsphere delivery system was available for growth hormone that released the hormone for 2 weeks after injection.

Therapeutic proteins or peptides have short half-life of minutes in a human body and are easily denatured at the hydrophilic-hydrophobic interface. It is therefore very difficult to develop an efficient drug delivery system for extended release of the therapeutic proteins in vivo. For example, U.S. Pat. Nos. 6,586,011 6,616,944, and 5,019,400 discloses processes of preparing micropheres for delivering proteins by spraying lactide-glycolide based polymers into a freezing liquid. However, this process has a serious drawback of the deterioration in activity of protein drug due to the hydrophobicity of PLGA and organic solution. U.S. Pat. No. 6,616,944 discloses a process comprising steps of introducing to PLGA polymer a functional group capable of forming an ionic bond with a protein and loading a protein drug to provide a protein drug-nanoparticle composite. However, this process causes polymer degradation and protein deterioration. Hydrogel based protein delivery systems have also been developed but show high initial burst of the drug instability over time and uncontrolled biodegradability.

An implantable osmotic pump system reportedly delivers peptide drugs at a constant rate for up to 1 year [J. C. Wright, et al., *Proc. Int. Symp. Controlled Release Bioact. Mater.* 24, 59 (1997)]. This pump can be loaded with an aqueous solution of a stabilized protein which is constantly released through an orifice for a predetermine time period. Similar reservoir implantable delivery systems for peptides and proteins have been reported during the past three decades. In one system, LHRH analogs have been loaded in a sealed non-degradable HEMA hydrogel cylinder where LHRH was constantly released for over one year both in vitro and in vivo.

While these reservoir systems showed to be most effective in releasing the protein for months at a zero order kinetics will no degradation of the loaded protein, these systems did not find broad clinical applications due to the need for a surgical procedure for implanting the device and the need to retrieve the device after depletion of the loaded drug.

OBJECTS AND BRIEF SUMMARY OF THE PRESENT INVENTION

A broad object of the present invention is to provide a delivery device and method for delivering bioactive agents in general, and drugs in particular, to internal tissue in a body having advantages in one or more of the above respects.

According to a broad aspect of the present invention, there is provided a delivery device for delivering a bioactive agent to internal tissue in a body, comprising: an inflatable balloon designed and dimensioned: to be introduced into the body in a deflated condition; to receive a quantity of the bioactive agent to be delivered; to be inflated while in the body through a port at one end of the balloon; and to deliver the bioactive agent within the balloon to the tissue in the body.

According to another aspect of the present invention, there is provided a method of administering a bioactive agent to internal tissue in a body, comprising: introducing a balloon in a deflated condition into the body; inflating the balloon; introducing the bioactive agent into the balloon at the time of, after, or before the inflation of the balloon; and delivering the bioactive agent from the balloon to the tissue.

The invention is described below with respect to a number of embodiments.

According to further features in the described embodiments, the inflatable balloon is made of a biodegradable material and is formed with micropores for times delivery of the active agent to the tissue.

According to further features in some described embodiments, the device further includes an inflating tube passing through the port for inflating the balloon after introduced into the body. The inflating tube is closed at one end and is formed with orifices adjacent its closed end for inflating the balloon. The inflating tube is closed by a plug fixed to the end of the tube by an inturned rim formed at the end of the tube received within an annular groove formed in the plug.

The inflating tube may be closed at one end by a plug of biodegradable material, or a plug having a one-way valve.

In some described embodiments, the balloon includes an inner balloon within it, or another balloon at the side thereof, both of the balloons being designed to receive two different bioactive agents. Both balloons are made of biodegradable material and are formed with micropores for the timed delivery the respective bioactive agents. In one described embodiment, both the inner and outer balloons are formed with small-sized micropores, while the inner balloon is further formed with larger-sized micropores.

In another described embodiment, the balloon is porous on one side, and is non-porous on the opposite side, such that the bioactive agent is delivered to tissue in contact with the porous side of the balloon.

As will be described more particularly below, the invention thus provides a biodegradable reservoir delivery system that may be inserted in the body by a trocar or a needle, inflated in the body with the drug solution or dispersion at the time of administration and thereafter eliminated from the body after the drug has been released. In such system, the drug release is through the balloon walls made from a biodegradable polymer having a predetermined permeability that fits the desired release rate for a certain small or large drug molecules. The delivery system of this invention is particularly useful for the controlled release of bioactive sensitive protein, DNA or polysaccharide for periods from weeks to months with safe complete elimination of the delivery carrier from the body. This system is of particular interest for veterinary applications where a large balloon can be inserted under the skin or at any tissue in the body using endoscopic devices and release the drug for long time periods.

For protein delivery or a sensitive drug, a stable solution or suspension of the drug should be prepared to be incorporated in the device. Stabilizing proteins in aqueous solutions is known for many clinical proteins which are already delivered in an aqueous solution. For example EPO, interferons, growth hormones and monoclocal antibodies have stable aqueous solutions.

The invention may thus be used to provide a biodegradable delivery system that: is formed in situ by balloon inflation using a needle or catheter; contains a reservoir loaded with an aqueous solution of an active agent; provides a constant release of a active agent or agents for periods of from a few days to a few months; that stores and releases sensitive drugs including peptides and proteins in its active form; and/or safely absorbs the body after releasing its agent. The delivery system may be made from biodegradable materials that do not invoke any side effects and that retains the incorporated agent in its active form during its storage and release period;

The active agent may be in aqueous solution, or in a gel form, or pre-encapsulated in a microspheres, or one can convert into a gel or a solid while in the patient body. The delivery system may be one wherein a collapsed balloon is loaded with powder of the stabilized drug or protein and salts that upon insertion in the body, absorb water from the surrounding tissues for osmotic calibration and release of the drug over time via the balloon walls.

The balloon may be made of a polymer selected from the group consisting of biodegradable hydroxyl-polyesters made from hydroxyl alkanoic acids and copolymers and blends thereof. Of particular interest are homo and copolyesters made from lactic acid, glycolic acid and caprolactone. The preferred polymers are those that are in clinical use that have already shown to be safe with predictable biodegradability, i.e. polylactide, poly(lactide-glycolide), poly(lactide-caprolactone) and polycaprolactone. The selected polymers for making the balloons of this invention should fit the desired mechanical and physical stability of the balloon in vivo.

For example, for a balloon that should retain its mechanical and physical consistency for two months in the body, a biodegradable polymer that keep its mechanical and physical properties when designed in a thin layer balloon, for at least one week, preferably one month and more preferably two months or longer. In addition, the polymers should be film forming and flexible enough to allow wrapping the balloon into a thin configuration that can be inserted within a tube that serves as dispenser for the balloon in vivo. The properties of the polymer compositions can be tailored to fit the requirements of this invention by either blending various polymers, mixing the polymer with hydrophobic or hydrophilic additives that alter the polymer properties. Such additives can be plasticizers that increase the flexibility of the balloon, hydrophilic components such as poly(ethylene glycole) and minerals that increase hydrophilicity and serve as pore making agents. Hydrophobic components can be triglycerides, fatty acids and esters and other biodegradable polymers. The polymer structure and molecular weight play a significant role in designing the desired properties of the polymer composition.

The present invention successfully addresses the shortcomings of the presently known configurations by providing a device system and method which can be easily used in constant drug, including peptides proteins and DNA and RNA based active agents release over time.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The device of the invention can be degraded in the body to chemically nontoxic and non-irritating components. The invention require two types of constructs that build the device, an inflatable biodegradable balloon, and a gel that is loaded within the balloon for inflating in the proper site of treatment. The balloon polymer composition requires flexibility and mechanical stability to allow insertion in the active site, inflated with an aqueous solution of the drug that either remain liquid or gel thereafter. The balloon should degrade at a predictable time period. The gel should be a liquid at time of application which solidify into a gel shortly after deposition into the balloon.

Polymers are provided which are bioabsorbable, biocompatible, and have mechanical properties suitable to hold the pressure and remain the structure of the spacer between tissues. The consistency of the gel may be from viscous semisolid to a solid. In another preferred embodiment, the polymers are fabricated into medical devices using standard polymer processing techniques.

The polymers described herein may be prepared by synthetic or natural methods. However, the method must provide the desired polymer in a form sufficiently pure for use as an implantable material. The polymer should not contain any undesirable residues or impurities which could elicit an undesirable response either in vitro or in vivo. The biodegradable balloon and/or gel are manufactured of materials with a predictable degradation rate and are calculated, to act as a local physical spacer for enough time necessary for the local therapy.

When the device is to be left in the body for long period, the balloon or chamber might be provided with a biodegradable one-way valve means, in cases in which it is filled with a liquid or gel, in order to prevent its deflation. The catheter is detached from the inflated balloon and the catheter or needle is removed, leaving the balloon in place.

The invention require one or two types of biodegradable components to construct and build the device, an inflatable biodegradable balloon, and a gel that is loaded within the balloon for inflating in the proper site of treatment. The balloon polymer composition requires flexibility and mechanical stability to allow insertion in the active site, inflated with an aqueous solution that gel thereafter. The balloon and the gel should degrade at a predictable time period. The gel should be a liquid at time of application which solidify into a gel shortly after deposition into the balloon.

Any liquid can be utilized to expand the balloon, preferably the liquid utilized is biocompatible and physiological such as 0.9% saline, Ringer solution or Hartman solution. Use of a physiological liquid is particularly advantageous in that it provides a good sonographic window which is essential in procedures that necessitate ultrasound guidance for introduction of the balloon or for local therapy or follow up (e.g. trans rectal ultrasound for therapy of the prostate). Additionally, in case of side effects such as pain or discomfort or local infection the balloon can be easily collapsed using a thin needle. It is essential that the drug to be loaded in the balloon will be soluble or well dispersed in the filling liquid. The liquid can be a hydrophilic or an hydrophobic paste.

While aqueous solutions are preferred for filling the balloon, non-aqueous solutions or dispersions are also considered. For example, a drug dispersion in a pharmaceutically acceptable oil such as Migliol medium chain saturated triglycerides, corn oil, olive oil and other fatty liquids that are used for injection can be loaded in the balloon. A dispersion or solution of water sensitive small molecular drugs as well as macromolecular drugs like proteins, polysaccharides and nucleotides can be used. The hydrophobic medium protects the drug from exposure to water, only the drug molecules that reach the close layer to the balloon wall are dissolved and diffuse out of the balloon. Besides serving as protecting shield for the bioactive agent to be delivered, another advantage of such hydrophobic media is keeping the device at its size until burst and slower hydrolytic degradation of the balloon as it is exposed only from the outer side to the hydrolysis process. The drug release can be manipulated by the type of oil, the particle size and density of the drug particles, surfactants added to the oil, preencapsulation of the drug, additives and stabilizers that may be added. At time when the balloon is eventually ruptured, the oily component is safely eliminated from the body in a similar way as any oily injection is absorbed. This approach is particularly useful for the delivery of growth hormone, erithropoetin, monoclonal antibody type of therapies, vaccines and other bioactive proteins that is in clinical use or to be in clinical use.

Similarly, the bioactive agent can be dispersed or dissolved in an emulsion, dispersion of liposomal formulation or drug loaded microspheres and combinations thereof. for the purpose of manipulating the release characteristics and stabilization of the active agent or agents. Needless to mention that more than one agent can be released from the balloon where each agent can be pre-treated so that the release is predetermined for each agent.

In the liquid expansion configuration, the balloon is preferably constructed from a fluid impermeable material such that an expanded state thereof can be retained following filling. Examples of suitable liquids include, but are not limited to, water, saline and the like.

As is mentioned above, the liquid can include agents that can be useful in imaging, radiation and/or thermal treatment modalities. For example, to enhance imaging, the liquid in balloon can include imaging contrast agents such as iodinated or baritated substances or various fluorocarbons, which are useful in fluoroscopy or CT scanning; echogenic or anechoic substances which are useful in ultrasound imaging, MRI contrasts agents such godolinium, radioactive isotopic substances for SPECT, or PET scanning. To protect tissue from radiation, agents such as iodinated substances, baritated substances, fluorocarbons, and the like can be included in the liquid. Agents active in tissue healing/repair can also be added to the liquid in which case, balloon is preferably constructed so as to enable release of such agents to the tissue. It will be appreciated that the above described agents can alternatively be added or incorporated into the material of the balloon in which case, such agents can be released upon degradation of the inner composition, or following absorption of a dose of treatment (e.g., radiation).

As is mentioned hereinabove, the device of the present invention is preferably inserted and positioned within tissue using a guide. Thus, according to another aspect of the present invention there is provided a system which can be utilized for balloon installation. Such a system includes device and a guide which is detachably attached to device. The guide serves to insert and position device and to expand the balloon when in position.

The guide can be a thin catheter or a blunt tip needle (canula), of about 1-5 mm in diameter, preferably 1-3 mm in diameter. The guide posses a lumen through which a balloon-expanding fluid (or rigid element) can be conducted from a device such as a syringe. Balloon expansion can be monitored by using different imaging technique such as: direct view, transillumination, fluoroscopy, endoscopic or laparoscopic US, US, CT scan, MRI, endoscopic view, etc. The guide is preferably constructed from biomedical grade elastomer such as PVC or polyurethane.

In cases where device is left within the body, the guide is detached from the device which preferably remains inflated by self sealing. Such self-sealing can be effected by a one way valve incorporated into the balloon neck, by viscosity of a balloon expanding liquid (e.g. one that forms a gel) or by a biodegradable sealing mechanism such as that described below. A cutting catheter made from bio-compatible material and having a sharp edge may be used to detach device from the guide if necessary.

Polymers are provided which are bioabsorbable, biocompatible, and have mechanical properties suitable to hold the pressure and remain the structure of the space between tissues. The consistency of the gel may be from liquid, viscous semi-solid to a solid. In another preferred embodiment, the polymers are fabricated into medical devices using standard polymer processing techniques.

The polymers may be prepared from any combination of monomeric units or from natural semi-synthetic and synthetic biodegradable polymers and compositions. These units must, however, be capable of biodegrading in vivo to non-toxic compounds, which can optionally be excreted or further metabolized.

The combination of units in the polymer must also be biocompatible, and not elicit an undesirable biological response upon implantation. The polymer may be biodegraded in vivo by any means, including hydrolysis, enzymatic attack, a cell-mediated process, or by any other biologically mediated process. It is considered desirable for tissue spacing applications that the polymer gel serve as a component in a temporary spacer construct, and thus be fully degraded once the spacer is not needed for protecting the patient tissue. Since the need for spacing activity may vary depending on type and duration of treatment, it is desirable to have polymers with a range of degradation rates as well as a range of different properties. Generally, however, preferred polymers will degrade in a matter of weeks to months, preferably less than one year.

The mechanical properties of the polymer are designed to meet the needs of the particular tissue engineering application. Thus, according to the method described herein for preparing bioabsorbable biocompatible polymers, the monomeric units can be selected to provide upon combination of the correct ratios of these monomeric units the desired property or property set. If necessary, the monomeric units may be combined in a specific order as in, for example, a block copolymer, or alternatively they can be assembled in a random manner. They may also be prepared with different molecular weights to achieve the correct performance. It should be noted that for the purpose of drug release it is not necessary that the balloon chamber is fully inflated or that there is a higher pressure inside the balloon. It may well be advantageous that the balloon is not fully inflated so that the risk for blow-up is reduced. Also, it is preferred that the drug loaded balloon device is installed in sites in the body that do not apply constant or sporadic pressure on the balloon to reduce the risk of blow-up and burst release of the loaded drug.

In a preferred method as described herein, the monomeric units are hydroxy acids, and the polymers are polyesters. The hydroxy acids may optionally contain other functional groups and be substituted at any position, including heteroatoms between the hydroxy and acid groups. These hydroxy acids may be polymerized either using synthetic methods or preferably using biological methods. In the latter case, the hydroxy acids may be derived in vivo from a non-hydroxy acid source.

Suitable methods for preparing the polyesters are described in Williams, S. F. and Peoples, O. P. CHEMTECH, 26:38-44 (1996), Hocking, P. J. and Marchessault, R. H. "Biopolyesters", G. J. L. Griffin, Ed., "Chemistry and Technology of Bioabsorbable Polymers," Chapman and Hall, London, 1994, pp. 48-96;

The bioabsorbable biocompatible polymers are polyesters including one or more linkages in the main polymer chain which are not ester linkages. These linkages should be susceptible to cleavage in vivo. Suitable non-ester linkages may include amides, urethanes, carbonates, iminocarbonates, oxalates, oxamates, orthoesters, anhydrides, phosphazenes, glycosides, and ethers. Incorporation of such chemistries can be used to alter biodegradation rates, tailor mechanical, surface, or other properties of the polymer, improve processibility and handling of the materials, and/or to provide methods for attachment of other compounds to the polymers.

Balloon can be prepared by dipping an inflated balloon made from stable polymers into a biodegradable polymer solution. After solvent evaporation a polymer coating onto the balloon is obtained. The internal balloon is deflated and the biodegradable balloon is separated. This biodegradable balloon is used for spacer formation by inserting the balloon into the desired location in the body by means of catheter and inflated with the gel forming solutions described above. The balloon loaded with the gel may remain in the site for periods of weeks, depending on the balloon polymer composition, thickness of wall and other common parameters that affect polymer degradation. The balloon degradation is affected from the outside by the body tissue and liquids and from the inside by hydrolysis occur by the gel solution.

Typical polymers suitable for balloon formation include: D,L-polylactide, lactide-glycolide copolymers, PEG-PLA copolymers, and polyesters and polyamides and other biodegradable compositions that form a strong film that can hold the shape for a desired time periods, weeks to a few months.

The time required for a polymer to degrade can be tailored by selecting appropriate monomers. Differences in crystallinity also alter degradation rates. Actual mass loss only begins when the polymer matrix degrade to oligomeric fragments that are small enough to be water soluble. Hence, initial polymer molecular weight influences the degradation rate.

Degradable polymers containing water-soluble polymer elements have been described. Sawhney et al., (1990) "Rapidly degraded terpolymers of dl-lactide, glycolide, and .epsilon.-caprolactone with increased hydrophilicity by copolymerization with polyethers," J. Biomed. Mater. Res. 24:1397-1411.

The biodegradable balloon and/or gel are manufactured of materials with a predictable degradation rate and are calculated, to act as a local physical spacer for enough time necessary for the local therapy. For example, during cryotherapy and thermal ablation this time might be a few hours, during external beam radiation this time might be 5 to 6 weeks, during brachytherapy it may be a few months and so on.

Further features and advantages of the invention will be apparent from the description below.

BRIEF DESCRIPTION OF THE DRAWINGS

The invention is herein described, by way of example only, with reference to the accompanying drawings, wherein:

The invention is described herein, by way of example only, with reference to the accompanying drawings, wherein:

FIG. 1b is an enlarged fragmentary view of the encircled portion of FIG. 1a;

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1A:
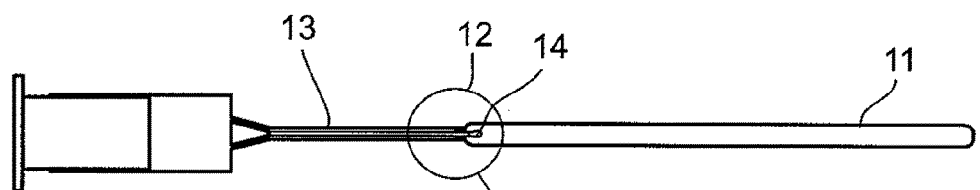
FIG. 1a schematically illustrates one form of bioactive agent delivery system constructed in accordance with the present invention.
Figure 1B:
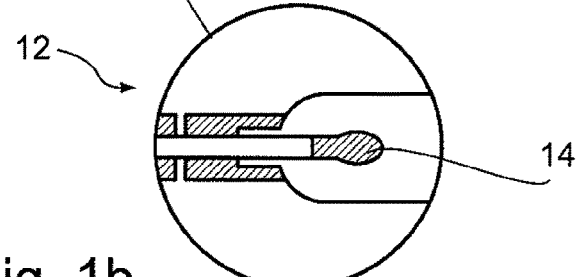

The device consists, FIG. 1, of a balloon 11 having an outer diameter ranging between 1 to 15 mm and preferentially ranging between 3 to 10 mm and having a length ranging between 1 to 30 mm and preferentially ranging between 5 and 10 mm. The balloon is releasably connected 12 to an inflation means 13, consisting of a tube or catheter, which may be rigid or flexible. A sealing mechanism is provided 14.

Figure 2:
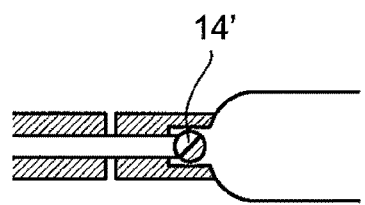
FIG. 2 schematically illustrates a variation in the construction of the plug in the delivery device of FIGS. 1a and 1b.

Such sealing mechanism may consist of one or more unidirectional valves FIG. 2 situated at the neck of the inflatable device. Alternatively, sealing may be by inflation with a biocompatible biodegradable gel.

Figure 3:
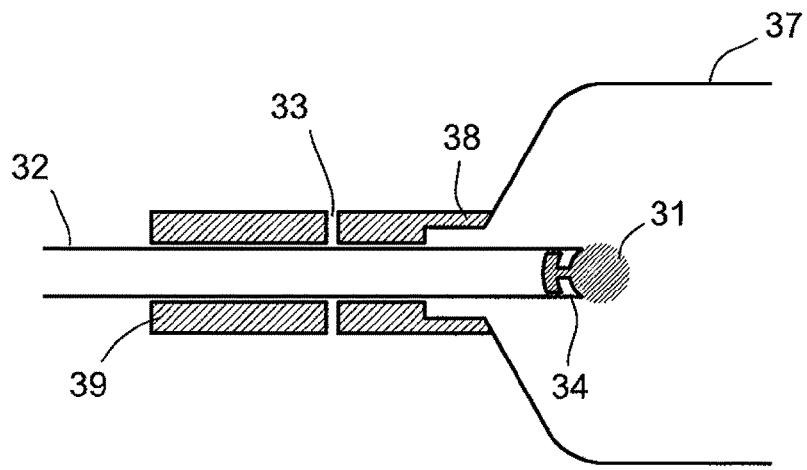
FIG. 3 schematically illustrates one manner of forming the balloon within an inflating tube containing a plug at its closed end.

In a preferred embodiment FIG. 3 the sealing mechanism consists of a plug 31 that is attached to the inflation tube or catheter 32. In this case, the inflation tube is provided with orifices 33 at its sidewalls for inflating the balloon. Preferentially, the inflation tube is provided with one or more depressions 34 at the lateral side 35 of its end 36 in order to increase the contact surface and the force that may be applied to the plug when sealing the balloon. The plug is preferentially pear shaped, or has a shape such that its free end is larger than the end attached to the inflation member. The balloon 37 is provided at its neck 38, with a rigid ring 39, or tube. The inflation member passes through this rigid tube or ring and its end with the attached plug is situated within the cavity of the balloon.

Figure 4A:
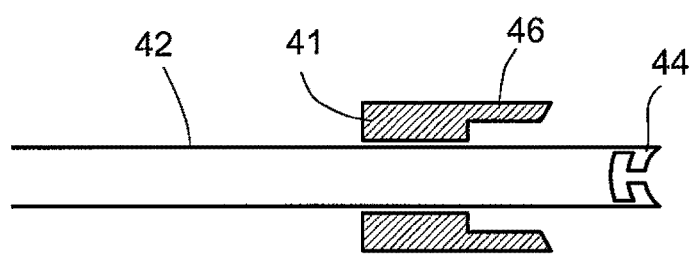
FIGS. 4a-4c illustrate the steps in forming the balloon in the delivery device of FIG. 3.
Figure 4B:
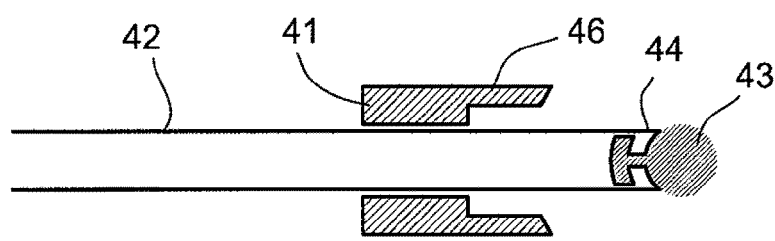
Figure 4C:
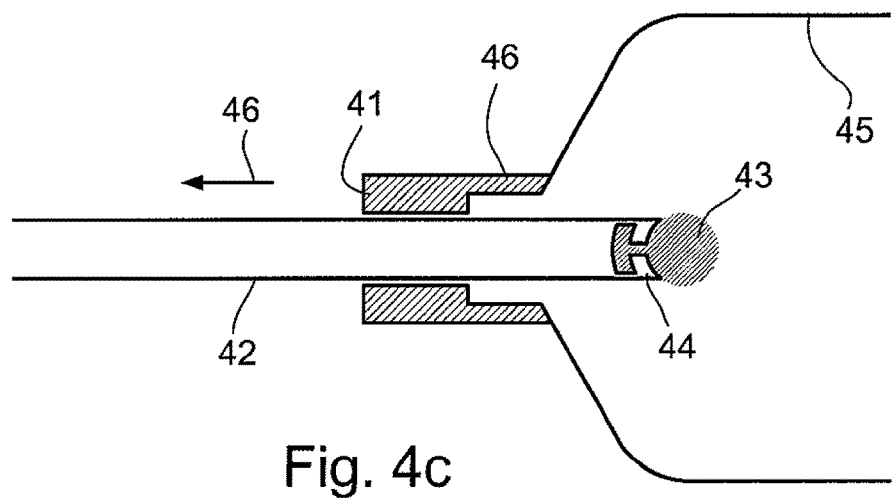

An assembling method of this device is described FIG. 4A-4C. The balloon is manufactured, preferentially by dip molding. The balloon is preferentially a seamless balloon made from biocompatible, biodegradable synthetic materials such as but not limited to: PLA, PLGA, poly-caprolactone, polydiaxone, or any combination thereof. Alternatively, it may be manufactured from biologically derived biodegradable materials such as collagen, etc.

The rigid tube or ring 41 is shown being casted on the shaft 42 of the inflating member in FIG. 4A. Then the plug 43 is casted on the tip 44 of the inflating member as is shown in FIG. 4B. The rigid tube and plug are made of biocompatible, biodegradable materials as mentioned earlier. The rigid tube or ring is made first, because the plug has a larger diameter than the rigid tube or ring and it cannot pass through the ring 41. Then balloon 45 is casted such that its neck is attached to rigid tube or ring 41, as is shown in FIG. 4C. The result will be that the distal tip of the inflating member with the attached plug will be situated within the cavity of the balloon and the shaft of the inflating member passes snugly through the lumen of the rigid ring or tube that is attached at the neck of the balloon. Following the filling and inflating of balloon 45, shaft 42 is pulled off in the direction of arrow 46 thereby bringing plug 43 into the lumen of rigid tube or ring 41. Sealing is accomplished by minimal heating within neck 47 of balloon 45.

Figure 5:
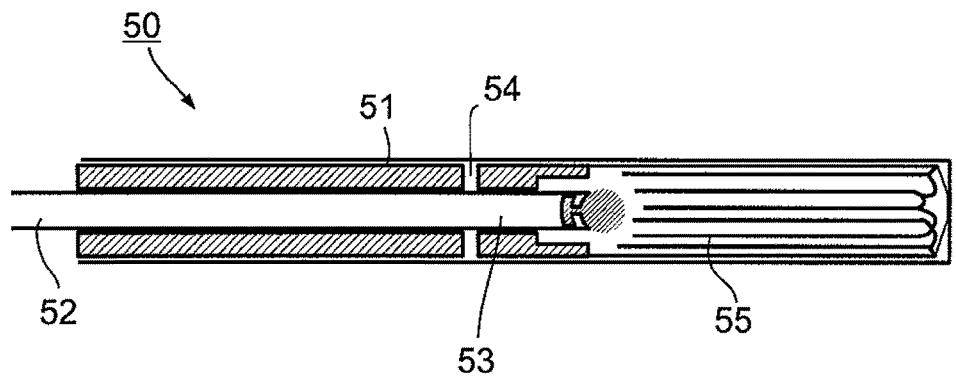
FIG. 5 schematically illustrates another bioactive agent delivery device constructed in accordance with the present invention.

A system is provided according to the invention for introducing, inflating, sealing the balloon and for detaching the inflation means, the distal end of which is shown in FIG. 5. The distal end of system 50 consists of sheath 51 surrounds inflation means 52 whose distal end 53, abuts against the rigid ring or tube 54 of the balloon 55. Sheath 51 also surrounds balloon 55 which is shown folded.

Inflation of the balloon is performed by pressurizing a physiologic fluid such as saline, Hartman or Ringer solutions or any other biocompatible solutions, or a biocompatible biodegradable gel into its lumen. The inflating fluid, or gel may contain any drugs and preferentially, water soluble drugs including therapeutic peptides such as LHRH, somatostatin, proteins such as erythropoetin, fibroblast growth factor (FGF), vascular endothelial growth factor (VEGF), hepatocyte growth factor, angiogenin, transforming growth factor (TGF), tissue necrosis factor (TNF, e.g., TNF-[alpha]), platelet derived growth factor (PDGF), granulocyte colony stimulatory factor (GCSF), placental GF, IL-8, proliferin, angiopoietin, e.g., angiopoietin-1 and angiopoietin-2, thrombospondin, ephrin-A1, E-selectin, leptin and heparin affinity regulatory peptide., calcitonine, polysaccharides like heparins, and small drug molecules for treating cancer, infections and local anesthetics. These drugs are to be delivered for an extended time periods from days to weeks for localized treatment or for systemic administration.

The drugs may be stabilized for various periods of time using mixtures of salts, buffers, amino acids sugars, metal ions and other agents that are commonly used for stabilizing particularly proteins.

The drugs may be delivered to the inflatable chamber as a solution or they may be delivered as powder or, other solid formulation or as micro-particles in order to permit to maintain a constant concentration within the chamber for as long as possible.

The wall of the inflatable device may be manufactured with small orifices or pores that will permit the diffusion of the drugs that are contained in the inflatable chamber to be delivered at a predetermined rate. Such small orifices may range from the order of 0.1 nm to 1 micron. The concentration of such pores and their dimensions may be controlled by the manufacturing process. Such process may utilize incorporation in the polymer of molecules whose dimensions are those of the desired pores. Use of a solvent that can dissolve these molecules, and not the polymer that is incorporated in the wall of the inflatable chamber, may result in creation of such pores. A suitable polymer is PEG that may have various molecular weights and sizes. Water soluble agents that may serve as porogenic agent where they enhance the formation of diffusion channels within the balloon membrane may include components such as poly(ethylene glycol), polypropylene glycol) and their copolymers of various ratios and molecular weights, modified polysaccharides such as carboxymethyl cellulose, fast degradaing biodegradable polymers such as aliphatic polyanhydrides which upon water contact with the film may degrade into water soluble degradation products and form a channels in the film. The larger the molecular weight of the soluble porogenic agent, the longer it may take until the full capacity of channels are formed. Components that are insoluble in the polymer matrix or in the solution of the polymer where the balloon is made from may include fine powders of salts, small organic molecules such as amino acids, mono and oligosaccharides, glycols, ethanol amine and the like.

Alternatively, water insoluble components may be used to form the channels such as fatty acids and oils where they may diffuse out of the film at body temperature and body environment.

The balloon can be made of a single polymer or of multiple layers where each layer may be made of a polymer of different characteristics.

Another feature that can be used to control the release/diffusion through the balloon wall is to form holes on through the balloon walls by mechanical mechanisms, by laser or drilling. The size of the holes and the number will control the release from the balloon.

Another possibility is that the balloon may be flexible and elastic so that it will inflate to certain volumes where the larger the volume the porosity of the wall increases and allows higher release rate. This feature may be controlled over time to control the release so that in one period a higher release is obtained while is other periods the balloon is less inflated and a smaller rate of release is obtained. Altering the release can be achieved also by applying external forces such as ultrasound, heat, vibrations electrical current as the like. The effect might be reversible or permanent.

Sealing of the balloon is performed by pulling the inflation member with the attached plug against the rigid ring or tube provided at the balloon neck. Counterforce is provided during this maneuver by the inner sheath of the system whose distal rim abuts against the proximal rim of the rigid ring or tube. The plug is broken at the attachment with the distal end of the inflating tube during this maneuver and the remaining plug is forced against the distal rim of the rigid tube or ring partially deforming and being deformed by this rim and therefore being impacted within the lumen of the rigid ring or tube. The result is a complete seal of the balloon.

Figure 6:
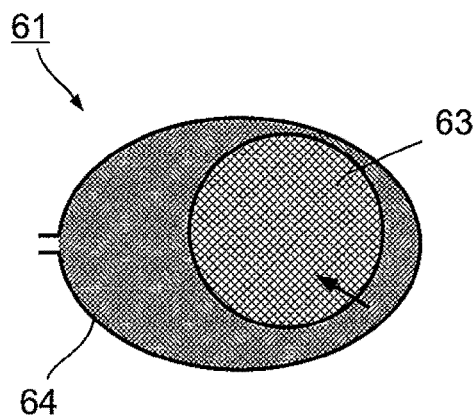
FIG. 6 schematically illustrates a variation wherein the delivery device includes two balloons for delivering two bioactive agents.

More than one substance may be introduced into such a device. Additionally, the wall of the device may be provided with pores of different sizes such that some of the pores are revealed only after a predetermined period of time. Such a design FIG. 6 may consist of a balloon 61 having dual layer wall one of which is inner wall 63 and the other is external wall 64. The external or both layers are made of a degradable material. Both layers are provided with small pores but only the inner layer is also provided with larger pores. Initially only small molecules can diffuse and pass through both layers. At a stage that a significant portion of the external layer has been degraded the pores of the inner layer will be exposed permitting also a controlled delivery of the second compound.

Additionally, the delivery of the compound and their rate may be regulated not only by the size of the pores but also by their shape and their electrical charge. Pores can be circular or elongated or strait though or winding through the wall cross-section. The wall can be made with inert biodegradable polymers or in combination with charged polymers or molecules such as chitosan, hyaluronic acid, carboxymethyl cellulose, and oxidized polysaccharides. Addition of charged molecules may result in a charged wall and pores whish may effect the diffusion through the wall. Holes through the balloon wall my change with time as a function of release of soluble components with the wall or gradual degradation of the polymer or polymers the balloon is made from.

Figure 7:
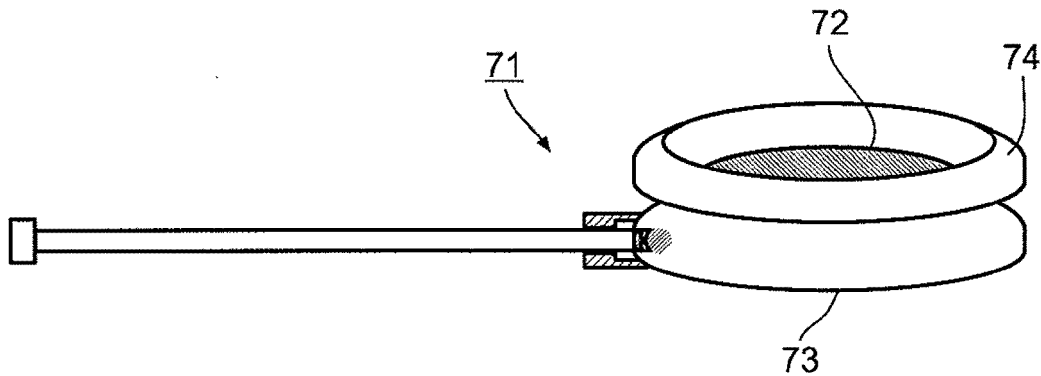
FIG. 7 schematically illustrates a variation wherein one side of the balloon is porous, two deliver the bioactive agent to the tissue with which it contacts, whereas the other side of the balloon is non-porous.

In another embodiment, the substances may be delivered in a particular direction. In FIG. 7, device 71 is shown, having two walls 72, 73. Only wall 71 is attached to a tissue that has to be treated. Optional inflatable ring 74 provides for better confining the disposed drug to a limited volume. Such tissue may be a tumor bed in which case a chemotherapeutic compound is released; or an inflamed tissue in which case an anti-inflammatory compound is released. In this case only the wall that is attached to the tissue 71 is provided with pores that may permit the diffusion of the substance.

Figure 8:
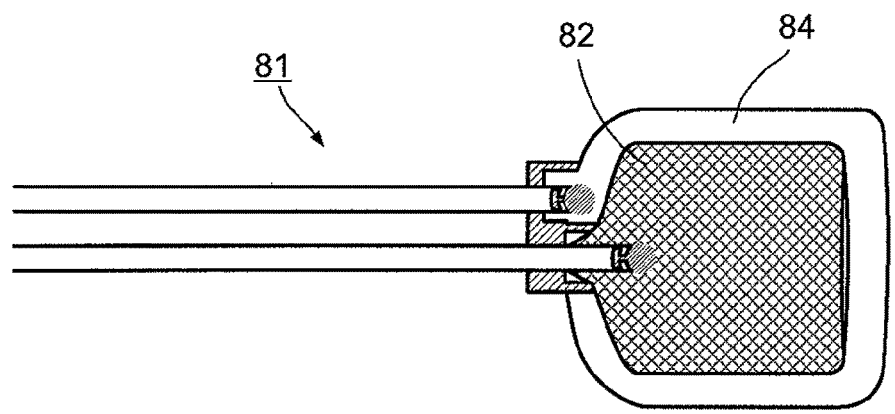
FIG. 8 schematically illustrates a delivery device introducing two balloons into an internal body cavity in a side-by-side relation, each to be filled with the same or different bioactive agents.

In another embodiment, shown in FIG. 8, device 81 is provided with two (or more) balloons 82, 84, to be located in side-by-side relation, each containing a bioactive agent to be delivered to the tissue contacted by the respective balloon. For example, in the case of a tumor, one substance may be an anti-tumoral agent that may be released from the balloon 82 that is in contact with such tissue, and a tissue protective substance may be released from the balloon 84 that is in contact with the healthy tissue that is to be protected. Alternatively, the two balloons may be filled with the same bioactive agents and constructed to release them in succession.

In another embodiment, one or more compounds are incorporated into the wall of the device. Such compound that may be incorporated into the polymers of the wall are those that may form pores of certain size and shape and number depending on the nature of the material added, its rate of solubility or degradability, melting point and other parameters which allow control of the diffusion through the balloon walls.

Such compounds may be incorporated into a particular wall of the device and the delivery of the substance will affect mostly the tissue that is adjacent to it. Different compounds may be incorporated into different walls, inducing different effects on different tissues according the position and orientation of the device. Additionally, different compound may be incorporated in different layer of the wall at a particular site of the device such that different compounds are released at different times from a particular region of the device.

Additionally, such a device may contain hydrophilic compounds that are introduced into the solution filling the inflatable chamber and other compounds that are incorporated into the wall of the device. Any combination such combination may be used.

In addition, other therapeutic compounds may be incorporated such as radioactive agents (examples). Radio-sensitizing substances examples or chemical ablative substances such as ethanol, acetic acid or hyperosmolar solutions.

Various sizes and shapes of the devices may be used. Additionally, the shape of the device may be tailored to the size and shape of the space in which it is intended to be introduced. Such shape and size may be determined preoperatively, for example before removal of a tumor from the pre-operative imaging study.

The device is introduced into the proper place that maybe subcutaneously or in other place using a needle or a guide wire. The deployment may be by inspection and palpation guidance for the subcutaneous position and by imaging means such as US, CT, MRI, SPECT, PET, fluoroscopy, endoscopy or other means for deeper positions.

Figure 9:
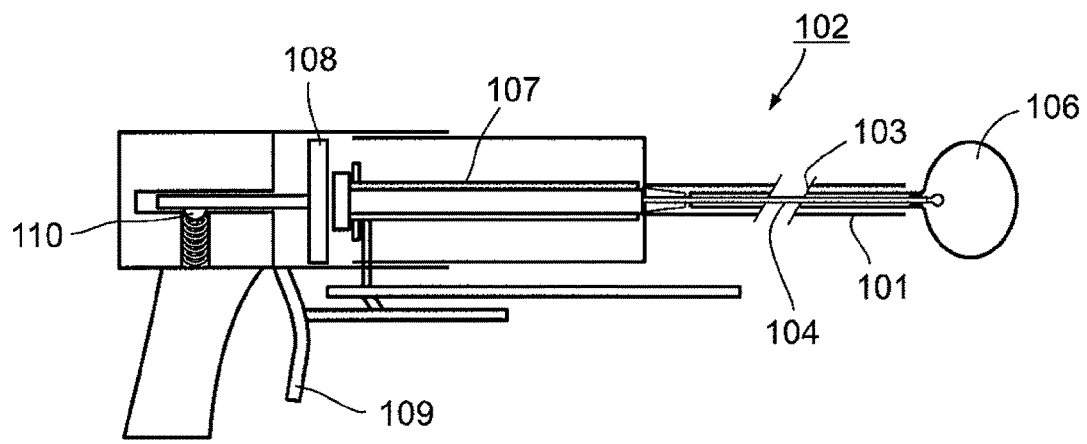
FIG. 9 schematically illustrates the use of a syringe for inflating a balloon within the body.

In the needle approach method, FIG. 9 a needle 101 is introduced and placed at the proper position. The device 102 having its balloon folded within delivery sheath 103. The distal end of the balloon is introduced to the proper position through needle 101. The needle and the sheath that envelops the folded balloon, not shown. Following the step of introducing both the needle and sheath are retracted revealing the balloon for its filling by pressurizing the active substance through the catheter 104. Pressurizing is accomplished by means of syringe 107 whose plunger is moved by rotating trigger 109. Safety catch 109 provides for securing the movement of plunger 108. Connecting tube 104 is detached from the balloon while sealing it as described hereinabove whereas the inflated member is left inflated in the tissue at the proper position.

Figure 10:
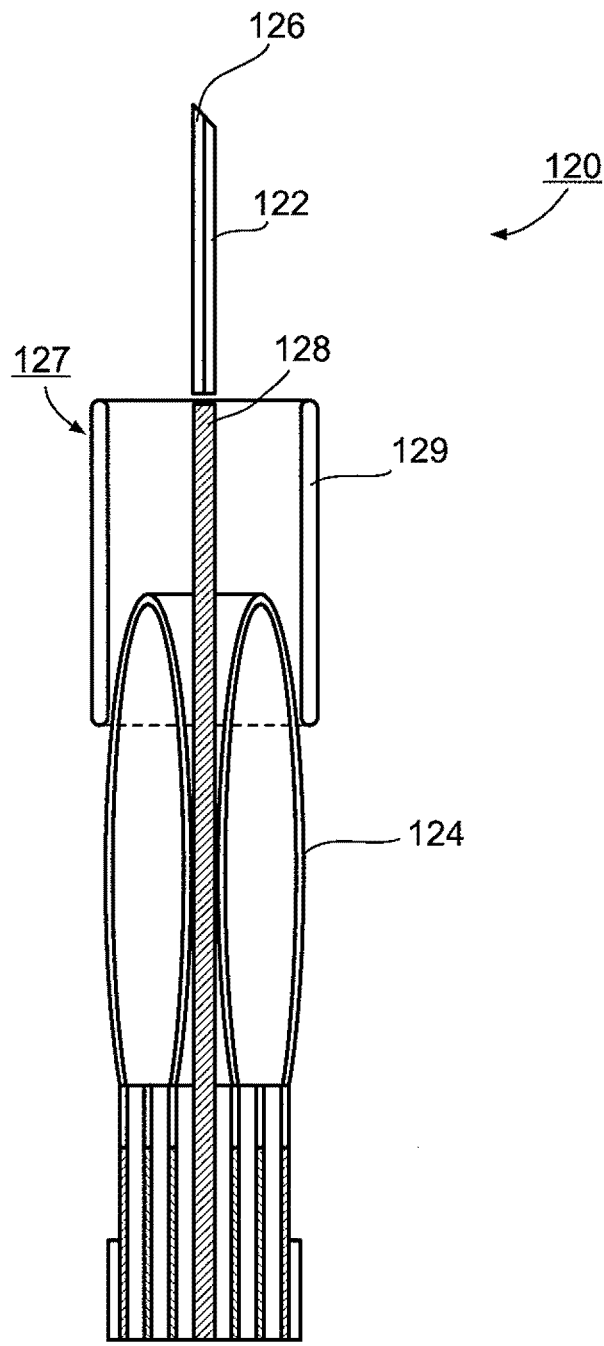
FIG. 10 schematically illustrates another manner, using a needle, guide wire, and trocar, for introducing a balloon into the body.

In the guide wire approach method, is schematically described in FIG. 10. Device 120 has a slender needle 122, which is introduced to place the distal end of balloon 124 at its desired position. Guide-wire 126, is introduced through the needle and the needle is removed. Dilator 127 comprising trocar 128, with a central channel and a sheath 114 are introduced over the guide wire to the proper position. The guide wire and the trocar are removed leaving the sheath of the dilator in the proper position. Balloon 124 is folded within a delivery sheath, not shown, such that it can be delivered to the proper position through dilator sheath 129. The dilator sheath and the sheath that envelops the folded device are further retracted thereby revealing the balloon to be further filled with the targeted compounds as is described hereinabove. The balloon in such a case is toroidally shaped when is being inflated.

Reference is now made to the following examples, which together with the above descriptions, illustrate the invention in a non limiting fashion.

EXAMPLES

Example 1

Balloon Fabrication

An important feature of the balloon of the present device is its ability to retain a predetermined shape once expanded. This feature is critical for optimal localized tissue pressure. For the same reason, the balloon of the present device is preferably fabricated with a smooth seamless external surface. To facilitate these requirements, a unique production process was formulated. The process combines two production concepts, a permutation of "lost wax" casting and dip molding.

Dip molding is used to "build" the balloon walls by dipping a pre-shaped model of the balloon in a solution made of a polymer dissolved in organic solvent. The pre-shaped model is made of materials that are later extracted from the internal volume of the balloon through its orifice. Unlike the well known "lost wax" casting method, wax cannot be used since it dissolves in organic solvents such as alcohols, chlorinated hydrocarbons, alkanones, acetonitrile, dialkyl ethers, cyclic ethers, acetate alkyl esters, and common aromatic solvents. Typical solvents are: butanol, dichloromethane, chloroform, butanone, acetone, acetonitrile, disisopropyl ether, tetrahydrofurane, dioxane, ethyl and butyl acetate, and toluene. The only casting agents that can be used are hydrophilic in nature protein, polysaccharides and various synthetic and semisynthetic polymers. Examples are: gelatin, agar, alginate, hydroxypropylcellulose, poly(acrylic acid-co-methylmethacrylate), chitosan, dextran, and arabinogalactane.

The balloon shape and size is based on the anatomy of the target location and the volume of the drug solution to be loaded in the balloon and to achieve minimal local pressure on the surrounding tissues/organs.

The following provides a stepwise description of the balloon production process of the present invention.

(i) Prepare a metal or plastic mold of the required balloon shape.
(ii) Inject hot casting agent (10% W/V agar in water) and wait 15 minutes for the cast to cool down and harden;
(iii) Remove balloon model from mold and attach to dip molding handle;
(iv) Dip the model inside the dipping solution (e.g. 10% W/V biodegradable polymer dissolved in an organic solvent) at a constant speed (~20 cm/min.)
(v) Repeat step (iv) several times until required coating thickness is obtained.
(vi) Wait until organic solvent completely evaporates (2-3 hours).
(vii) Extract casting agent through balloon orifice by placing the coated model in hot water (70° C.) and push out the content and rinsing the inner side of the balloon with hot water until a clear and clean balloon is obtained.

Alternatively, balloons are fabricated by welding or gluing together two films of the balloon material. "Pressure forming", "film extrusion" or "blown film" methods are used to prepare the films. The films are then welded along the balloon external path using an accurate and controlled ultrasonic energy or glued using an accurate deposit of organic solvent along the gluing path.

Example 2

Preparation of Diffusion Controlled Membranes and Balloons

Rate controlling membranes are prepared by either forming holes across the balloon walls by physical means or by adding porogenic agents that dissolve and released from the wall leaving desired pores across the wall where drugs can diffuse out at a controlled predetermined rate profiles. Moreover, the device is designed to remain intact and release its content at a later desired date either in a controlled manner or at a very short time. Several balloons made of different polymers, designs or wall thickness so that they release their content at different time periods at different rates and durations. A practical approach for inducing pore formation in a film is by incorporating a water soluble component (porogen) within the film which is removed after the film has been formed. The removal of the porogen can be prior to insertion of the device into the delivery device or can be formed when in contact with body fluids.

In a typical experiment, dichloromethane solutions of poly (caprolactone-L-lactide) 70:30 w/w, Mw=100,000 and polyethylene glycol Mw=400 (PEG400) and PEG2000 mixed at a 1, 5, 10 and 20 w/w % per polymer were used for producing balloons by dipping as described above. The balloons were immersed in water to allow the leach-out of the water soluble PEG. The balloons were analyzed for pore size, uniformity of pores throughout the membrane, and diffusion of LHRH hormone and BSA (bovine serum albumin) as representative protein. Uniform micron size holes of a similar size were generated for the 1 and 5% PEG but more holes for the 5%, while the 20% PEG generated much larger holes throughout the wall which also affects the strength of the wall. Balloons loaded with 10% w/v solutions of LHRH or BSA constantly released the proteins for periods of a few months from the 5% PEG and for weeks from the 20% PEG balloons where BSA was released for a longer time at low concentrations compared with the LHRH. For comparison, 5-FU—a water soluble anticancer agent released much faster for a shorter time period at a zero order profile. The balloon remain inflated for about 4 months in 0.1M phosphate buffer solution at 37° C. before signs of degradation occur measured by a significant decrease in molecular weight and change in the flexibility and clarity of the balloons. In a continuation experiment, lyophilized powder of LHRH (10 mg) on dextrose (100 mg) was dispersed in glycerol (100 mg) and injected into the 10 mm diameter balloon and release under physiological conditions was determined. Native LHRH was constantly released for weeks from the delivery system as determined by HPLC.

In a similar experiment, biodegradable balloons of 1 cm diameter were prepared from triblock copolymers of L-PLA-co PEG5000, Mw=80,000 or in a 50:50 mixture with L-PLA Mw=120,000 by the solvent casting on a gelatin mold method. Balloons with 200 and 300 micron wall thicknesses were prepared. These balloons swell when inserted in aqueous media to form hydrogel walls which are permeable to water soluble molecules. Small molecules including 5-FU and methotrexate were constantly release at high amounts for weeks while BSA was released at a very low level with LHRH being released at low concentrations over time.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A delivery device for delivering a bioactive agent to internal tissue in a body, comprising:
an inflatable balloon having a wall surrounding a cavity and formed of a biodegradable material and designed and dimensioned:
  (a) to be introduced into said body in a deflated condition;
  (b) to receive a quantity of the bioactive agent to be delivered within said cavity of said balloon;
  (c) to be inflated while in said body through a port at one end of said balloon; and
  (d) to deliver the bioactive agent within said balloon to said tissue in the body, in a sustained manner through said wall;
wherein said inflatable balloon wall is prepared using porogenic agents for forming pores across said wall, and, using a solvent for dissolving said porogenic agents and not said biodegradable material.

2. The device according to claim 1, wherein said inflatable balloon wall is formed with micropores having a size range between 0.1 nm and 1 micron for delivery of the bioactive agent from said balloon cavity to said tissue in the body.

3. The device according to claim 1, wherein said bioactive agent is a small molecule drug of a bioactive peptide or a protein, a bioactive polysaccharide, a bioactive oligonucleotide or polynucleotide.

4. The device according to claim 1, wherein said bioactive agent is a therapeutic agent other than a drug, including herbal medications and homeopathic remedies.

5. The device according to claim 1, wherein said bioactive agent is in a flowable form and is introduced under pressure into said balloon while in said deflated condition in the body.

6. The device according to claim 1, further including an inflating tube passing through said port for inflating said balloon after introduced into the body.

7. The device according to claim 6, wherein said inflating tube is closed at one end and is formed with orifices adjacent to its closed end for inflating said balloon.

8. The device according to claim 7, wherein said balloon is closed by a plug located at an inflation port thereof.

9. The device according to claim 8, wherein said plug includes a one-way valve.

10. The device according to claim 1, wherein said balloon includes an inner balloon within it; and wherein both of said balloons are designed to receive two different bioactive agents, are microporous for the timed delivery of both bioactive agents, and are made of biodegradable material.

11. The device according to claim 10, wherein both balloons are formed with small sized micropores, and wherein said inner balloon is further formed also with larger sized micropores.

12. The device according to claim 1, wherein said balloon is porous on one side, and is non-porous on the opposite side, such that the bioactive agent is delivered to tissue in contact with said porous side of said balloon.

13. The device according to claim 1, wherein there are two of said balloons, each receiving a quantity of a bioactive agent, said two balloons being dimensioned to be introduced into said body in side-by-side relation and to deliver said bioactive agents in succession.

14. The device according to claim 1, wherein said inflatable balloon is made of a polymer selected from the group consisting of biodegradable hydroxyl-polyesters.

15. The device according to claim 14, wherein a said hydroxyl-polyester is made from caprolactone.

16. The device according to claim 2, wherein said micropores are formed using a chemical process.

17. The device according to claim 1, wherein said balloon wall is flexible enough to allow folding and wrapping said balloon into a thin configuration that can be inserted within a tube.

18. The device according to claim 1, wherein said balloon wall is seamless and is configured to inflate to an outer diameter in the range of 3 to 10 millimeters.

19. The device according to claim 1, wherein said balloon wall and the bioactive agent are selected to define a predetermined release rate of the bioactive agent from said balloon cavity for a period of at least 1 week.

20. The device according to claim 1, wherein said solvent includes water.

21. The device according to claim 1, wherein said inflatable balloon is prepared by a procedure comprising:
   forming a balloon model of a required balloon shape;
   dipping said balloon model into a solution of a biodegradable polymer dissolved in an organic solvent;
   evaporating said organic solvent, thereby obtaining a polymer coating having said required balloon shape on said balloon model; and
   rinsing inner side of said balloon model coated with said polymer coating, for dissolving and separating said balloon model from said polymer coating, thereby obtaining said inflatable balloon.

22. A delivery device for delivering a bioactive agent to internal tissue in a body, comprising:
an inflatable balloon having a wall surrounding a cavity and formed of a biodegradable material and designed and dimensioned:
   (a) to be introduced into said body in a deflated condition;
   (b) to receive a quantity of the bioactive agent to be delivered within said cavity of said balloon;
   (c) to be inflated while in said body through a port at one end of said balloon; and
   (d) to deliver the bioactive agent within said balloon to said tissue in the body, in a sustained manner through said wall;
wherein said inflatable balloon wall is formed with micropores having a size range between 0.1 nm and 1 micron for delivery of the bioactive agent from said balloon cavity to said tissue in the body; and
wherein said micropores are formed using a chemical process.

23. The device according to claim 22, wherein said balloon wall is flexible enough to allow folding and wrapping said balloon into a thin configuration that can be inserted within a tube.

24. The device according to claim 22, wherein said balloon wall is seamless and is configured to inflate to an outer diameter in the range of 3 to 10 millimeters.

25. The device according to claim 22, wherein said balloon wall and the bioactive agent are selected to define a predetermined release rate of the bioactive agent from said balloon cavity for a period of at least 1 week.

26. A delivery device for delivering a bioactive agent to internal tissue in a body, comprising:
an inflatable balloon having a wall surrounding a cavity and formed of a biodegradable material and designed and dimensioned:
   (a) to be introduced into said body in a deflated condition;
   (b) to receive a quantity of the bioactive agent to be delivered within said cavity of said balloon;
   (c) to be inflated while in said body through a port at one end of said balloon; and
   (d) to deliver the bioactive agent within said balloon to said tissue in the body, in a sustained manner through said wall;
wherein said inflatable balloon is prepared by a procedure comprising:
   forming a balloon model of a required balloon shape;
   dipping said balloon model into a solution of a biodegradable polymer dissolved in an organic solvent;
   evaporating said organic solvent, thereby obtaining a polymer coating having said required balloon shape on said balloon model; and
   rinsing inner side of said balloon model coated with said polymer coating, for dissolving and separating said balloon model from said polymer coating, thereby obtaining said inflatable balloon.

27. The device according to claim 26, wherein said inflatable balloon wall is formed with micropores having a size range between 0.1 nm and 1 micron for delivery of the bioactive agent from said balloon cavity to said tissue in the body.

28. The device according to claim 26, wherein said balloon wall and the bioactive agent are selected to define a predetermined release rate of the bioactive agent from said balloon cavity for a period of at least 1 week.

* * * * *